US006162213A

United States Patent [19]
Stewart

[11] Patent Number: 6,162,213
[45] Date of Patent: Dec. 19, 2000

[54] MULTIPLE WAVELENGTH METAL VAPOR LASER SYSTEM FOR MEDICAL APPLICATIONS

[75] Inventor: Bob W. Stewart, Cincinnati, Ohio

[73] Assignee: Cincinnati Sub-Zero Products, Inc., Cincinnati, Ohio

[21] Appl. No.: 08/180,767

[22] Filed: Jan. 7, 1994

Related U.S. Application Data

[63] Continuation of application No. 07/792,286, Nov. 14, 1991, abandoned, which is a continuation-in-part of application No. 07/514,198, Apr. 25, 1990, Pat. No. 5,066,291.

[51] Int. Cl.⁷ .................................................. A61N 5/06
[52] U.S. Cl. .................... 606/10; 606/3; 606/13
[58] Field of Search ...................... 606/2–19; 607/88–92; 372/9, 23, 25, 56

[56] References Cited

U.S. PATENT DOCUMENTS

| | | | |
|---|---|---|---|
| 3,750,670 | 8/1973 | Palanos et al. | 606/4 |
| 3,988,593 | 10/1976 | Dewey, Jr. | 307/88.3 |
| 4,173,738 | 11/1979 | Boling et al. | 330/4.3 |
| 4,180,751 | 12/1979 | Ammann | 307/428 |
| 4,187,475 | 2/1980 | Wieder | 331/94.55 |
| 4,189,652 | 2/1980 | Levinos et al. | 307/428 |
| 4,213,060 | 7/1980 | Byer et al. | 307/426 |
| 4,295,104 | 10/1981 | Burnham | 331/94.5 C |
| 4,336,809 | 6/1982 | Clark | 606/3 |
| 4,455,657 | 6/1984 | Byer | 372/18 |
| 4,502,144 | 2/1985 | Suhre | 372/23 |
| 4,503,854 | 3/1985 | Jako | 606/13 |
| 4,520,816 | 6/1985 | Schachar et al. | 128/395 |
| 4,614,190 | 9/1986 | Stanco et al. | 128/395 |
| 4,639,923 | 1/1987 | Tang | 372/21 |
| 4,672,969 | 6/1987 | Dew | 606/8 |
| 4,739,507 | 4/1988 | Byer et al. | 372/22 |
| 4,791,927 | 12/1988 | Menger | 606/10 |
| 4,809,291 | 2/1989 | Byer et al. | 372/78 |
| 4,836,203 | 6/1989 | Müller et al. | 128/664 |
| 4,880,996 | 11/1989 | Peterson et al. | 307/425 |
| 4,891,043 | 1/1990 | Zeimer et al. | 606/2 |
| 4,931,053 | 6/1990 | L'Esperance, Jr. | 606/2 |
| 5,007,060 | 4/1991 | Hall | 372/23 |
| 5,180,378 | 1/1993 | Kung et al. | 606/3 |

FOREIGN PATENT DOCUMENTS

| | | | |
|---|---|---|---|
| 8706775 | 11/1987 | WIPO | 606/3 |

OTHER PUBLICATIONS

"Emissions Laser Infrarouges Dans Les Vapeurs De Thulium et D'Ytterbium" by Cahuzac; Physics Letters; vol. 27A No. 8 pp 473–4; Sep. 1968.

"An Investigation of a Discharge–Heated Barium Laser" by Bricks et al; J Appl Phys; vol 49, No. 1; Jan. 1978 pp 38–39.

An extension of the Three–Zone Model to Predict Dept of Tissue Damage Beneath ER:YAG and Ho:YAG Laser Excisions, Alan L. McKenzie.

Formation and Applications of Ring Profile Laser Beams, He Hailin, Oct, 1986 Chinese Physics–Lasers vol. 13, No. 10.

(List continued on next page.)

*Primary Examiner*—David M. Shay
*Attorney, Agent, or Firm*—Dinsmore & Shohl LLP

[57] ABSTRACT

A multiple wavelength laser system includes an active laser gain medium comprising metal vapor which, when excited, produces laser radiation at a plurality of wavelengths. A plurality of medically useable wavelengths are coaxially transmitted from the laser system for simultaneous use in a medical procedure. One of the wavelengths produced is closely matched to a light absorption peak of either water or Hemoglobin, and another wavelength is matched to the other of these light absorption peaks or a targeted photosensitive agent or chemical. The disclosed laser system can also include a laser gain medium comprising a plurality of metal vapors to produce the plurality of wavelengths desired. In preferred embodiments, the metal vapors can include barium, thulium, and/or samarium. A laser conversion device such as an OPO crystal may also be included to convert a portion of the radiation to one or more additional medically useable wavelengths.

30 Claims, 5 Drawing Sheets

OTHER PUBLICATIONS

Combination Studies on Hyperthermia Induced by the Neodymium Yttrium Aluminum Garnet (Nd:YAG) Laser as an Adjuvant to Photodynamic Therapy, Thomas S. Man, SPIE, vol. 847, pp. 158–162 *New Directions in Photodynamic Therapy* (1987).

Photodynamic Therapy Alone or in Conjunction with Near–Infrared Light–Induced Hyperthermia in Human Malignant Tumors. A Methodological Case Study, S. Andersson–Engels et al., SPIE, vol. 908, pp. 116–125 *Laser Interation with Tissue* (1988).

French Develop Four–In–One PDT Laser, *Laser Focus World*, Mar. 1990, pp. 95–96.

Bronochoscopic Phototherapy for Malignancies of the Tracheobronchial Tree, Eric S. Edell et al., *Laser in Medicine and Surgery*, pp. 137–141 (1987).

Medical Applications of Lasers, Thomas F. Deutsch, *Physics Today*, Oct., 1988, pp. 56–63.

Computer Controlled Contact Nd:YAG Laser System for Interstitial Local Hyperthermia and PDT, Norio Diakuzono et al. SPIE, vol. 907, pp. 75–79, *Laser Surgery: Characterization and Therapeutics* (1988).

An investigation of a discharge–heated barium laser, B.G. Bricks, T.W. Karras, and R.S. Anderson, *Journal of Applied Physics*, vol. 49, Jan., 1978.

Principles of Operations, 1978.

Analyses of Frequency Conversion and Applications of New Non–Linear Crystals, J.T. Lin.

Generation of 1.54 Micron Radiation from YAG–Pumped Raman Media and Non–Linear Crystals, J.T. Lin.

Laser Surger: CO2 or HF, Myron L. Wolbarsht IEEE Journal of Quantum Electronics QE 20, No. 12 Dec. 1984.

High Temperature Alumina Discharge tube for Pulsed Metal Vapor Lasers, *The Review of Scientific Instruments*, vol. 37, No. 7, Jul., 1966.

Emissions Laser Infrarouges Dand Les Vapeurs de Thulium et D'Ytterbium, *Physics Letters*, vol. 27A, No. 8, Sep. 9, 1968.

Emissions Laser Infrarouges Dans Les Vapeurs de Terres Rares, *Physics Letters*, vol. 31A, No. 10, May 18, 1970.

Nouvelles Raies Laser Infrarouges Dans la Vapeur de Baryum, *Physics Letters*, vol. 32A, No. 3, Jun. 29, 1970.

Self–Heated, Multiple–Metal–Vapor Laser, Theodore S. Fahlen, *IEEE Journal of Quantum Electronics*, Mar., 1976.

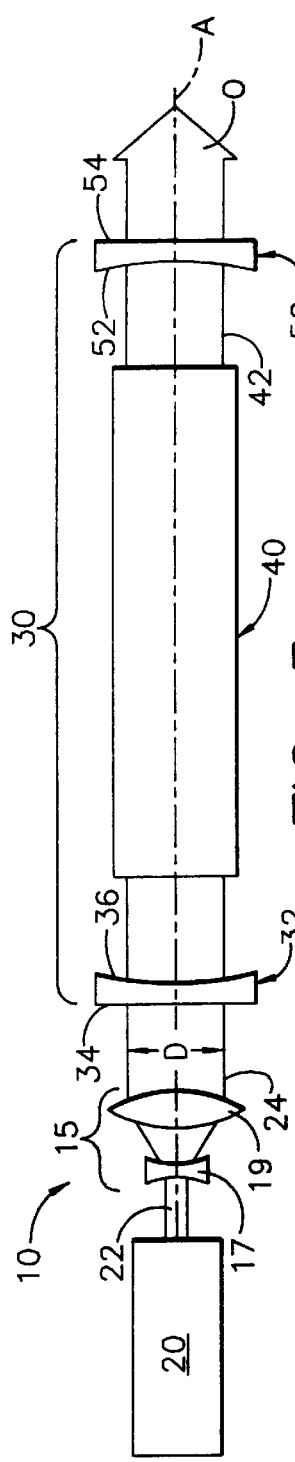
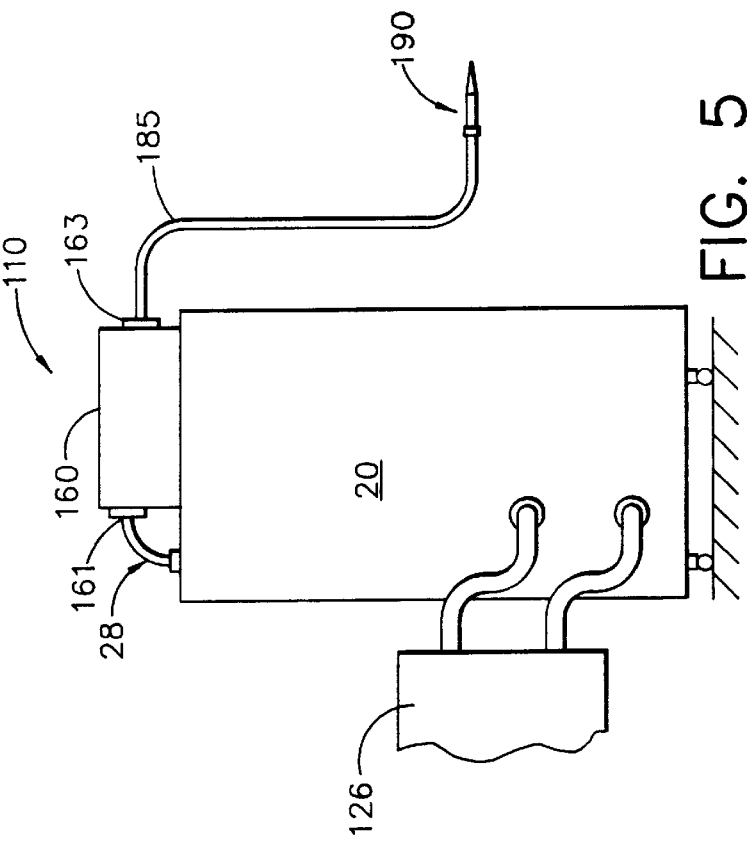
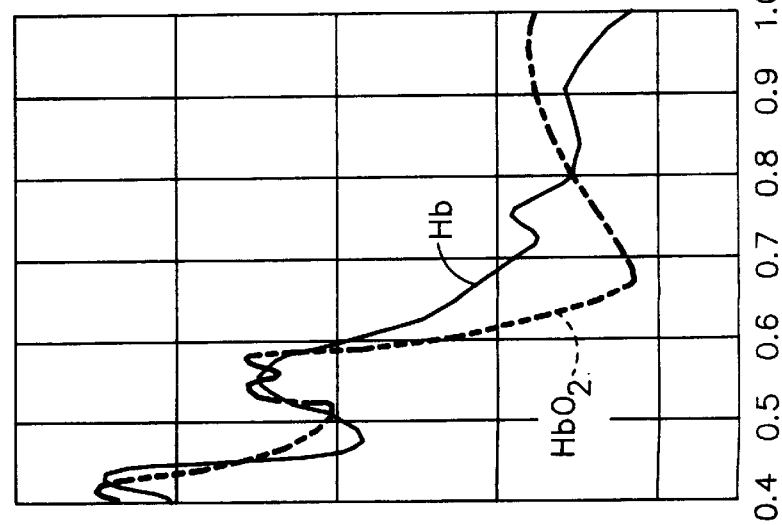

6,162,213

MULTIPLE WAVELENGTH METAL VAPOR LASER SYSTEM FOR MEDICAL APPLICATIONS

REFERENCE TO RELATED APPLICATION

This is a continuation, of application Ser. No. 07/792,286, filed Nov. 14, 1991 now abandoned. This is a Continuation-in-Part of application Ser. No. 07/514,198, filed Apr. 25, 1990, now U.S. Pat. No. 5,066,291, in the name of the present inventor, and entitled SOLID-STATE LASER FREQUENCY CONVERSION SYSTEM AND METHOD.

TECHNICAL FIELD

This invention relates to an apparatus and method for providing two or more predetermined wavelengths of laser radiation for coaxial transmission and simultaneous use, and, more particularly, to a metal vapor laser system for providing a single output laser light beam having a predetermined mixture of wavelengths for simultaneous medical use.

BACKGROUND ART

The development and use of laser systems in surgery and other medical applications continues to expand at an ever increasing rate as new technology becomes available and new applications for lasers are discovered. Currently used surgical laser systems include the $CO_2$ laser device which produces a light beam having a wavelength of 10.6 microns, and solid-state devices such as the Nd:YAG laser (Neodymium Yttrium Aluminum Garnet, $Y_3 Al_5O_{12}$) laser, which produces a light beam having a wavelength of approximately 1.064 microns, the argon-ion laser producing a light beam having a wavelength of approximately 0.5145 microns (or 514.5 nm), the Erbium:YAG (Er:YAG) laser producing a light beam having a wavelength of approximately 2.9 microns, the Holmium:YAG (Ho:YAG) laser producing a light beam having a wavelength of approximately 2.1 microns, and, more recently, a frequency-doubled Nd:YAG laser producing a light beam having a wavelength of approximately 0.532 microns (532 nm). Heretofore, however, the Er:YAG and Ho:YAG lasers have been being used mainly in experimental applications, as they have yet to obtain universal approval for clinical use.

It has been found that because human tissue is approximately 80%–90% water, the absorption of radiation energy (i.e. light energy) in water will determine the characteristics of laser interaction in tissue. The $CO_2$ laser has been found to provide a very good "light knife" due to its ability to induce incisions with less charring with good hemostatic control; however, the Nd:YAG laser has better photocoagulative ability, as its 1.064 micron wavelength penetrates much deeper into tissue than the 10.6 micron radiation, and is closer to the hemoglobin absorption peak (i.e. approximately 0.577 microns). Because the water absorption peak has been found to be approximately 2.9 microns, the Er:YAG laser is of special interest as providing an optimum "light knife" whose light beam wavelength is much closer to the absorption peak of hemoglobin (i.e. blood) than the $CO_2$ laser, and should theoretically provide better coagulative effects in conjunction with its superb cutting abilities. In practice, however, it has been observed that Er:YAG radiation is absorbed so strongly by the water content of the tissue that it provides very poor hemostasis.

On the other hand, it has been established by theory and experiment that a relationship exists between the time which tissue is exposed to light beam energy and the size of the surrounding zone of thermal damage caused by that light beam. It has been found that rapid, short "bursts" or "pulses" of laser light can help to minimize the surrounding zone of thermal damage caused by laser cutting. Because the Er:YAG laser technology is relatively new and immature, and because of the relatively longer wavelength of its output, efficient technology capable of providing short pulses of the output radiation is not available. In contrast, the relatively well developed technology of the Nd:YAG laser can provide electro-optical pulsing (Q-switched technology) which can be up to 100 times shorter than the relatively crude pulsing technology currently available for Er:YAG lasers. Similarly, reliable pulsing technology has yet to be developed for Ho:YAG lasers.

Consequently, while the Er:YAG and Ho:YAG lasers provide laser radiation at wavelengths much closer to the absorption peak of water, the inability to precisely control the temporal application of such laser radiation tends to result in increased thermal diffusion beneath the laser excision, which can result in increased inflammatory response within the tissue, delaying healing and increasing the chances of post operative infection. Another laser delivery system known as the HF laser can also product laser radiation at a wavelength of approximately 2.9 microns, however, the use of the HF laser in medical applications is felt by many to be inappropriate because of the large size of the device and the dangerous nature of the technology itself (HF lasers use flowing Sodium fluoride $SF_6$—a toxic gas—to produce free fluorine).

The 1.064 micron wavelength output of the Nd:YAG laser provides better coagulative features as a result of relatively deeper penetration into the tissue and resultant enhanced hemostatic control. On the other hand, a light beam at the 1.064 micron wavelength creates inferior incisions as increased charring of surrounding tissue is created. In fact, as the wavelength of a particular laser light beam is decreased toward the Hemoglobin absorption peak (i.e. between approximately 0.5 and 0.6 microns), the ability for hemostatic control increases, while the precision or "cleanness" of the incision decreases. While a particular laser can sometimes be chosen for optimum surgical conditions (such as in cornea surgery where there is no bleeding and optimal incision control can be obtained by utilizing a laser which produces radiation at a wavelength within the peak of the water absorption spectrum of 2.85 to 2.95 microns), too often a tradeoff must be made between the surgeon's desire to obtain the most precise and clean incision, and a desire to minimize thermal damage and to optimize hemostasis. Additionally, due to the relatively high cost of laser equipment, rarely does a physician have the luxury of choosing between several types of laser devices for any particular surgical procedure.

Because a variety of solid-state laser devices are available in the industry which provide laser radiation at wavelengths in the relatively longer ranges of the spectrum (i.e. 0.700–3.0 microns), it has not been uncommon to utilize available technology for doubling the frequency of the output of one of these devices to reduce the wavelength to the visible spectrum and/or to provide laser energy closer to the absorption peak of hemoglobin for increased hemostatic control. U.S. Pat. Nos. 4,639,923, 4,739,507, and 4,809,291 are examples of devices which provide for doubling of frequencies to reduce the wavelength of laser radiation provided by a particular laser device. While frequency doubling can reduce the resultant power provided by any particular laser device by up to 70% or more, this procedure often represents the only practical way of obtaining laser radiation to provide for visible laser light and/or increased hemostatic control.

For example, laser radiation from the Nd:YAG laser can be frequency doubled by utilization of well-known and relatively readily available KTP (KTiOPO$_4$) crystals or Beta-Barium-Borate (B-BaB$_2$O$_4$ or BBO) crystals to provide laser radiation at a wavelength of 0.532 microns. While laser radiation at a wavelength of approximately 0.577 microns can be provided with a dye laser system, this wavelength cannot be produced by currently available solid-state systems, which are much preferred for surgical application due to their reliability and ease of use and maintenance. Commercial "KTP" lasers, however, do not provide multi-wavelength beams simultaneously, but require switching between pump or converted wavelengths.

Optical parametric oscillator (OPO) technology has also been utilized to convert laser radiation to longer wavelengths in a more reliable solid-state form. U.S. Pat. No. 4,180,751 includes a description of the utilization of an OPO device to provide a signal or idler frequency from a pump wavelength. OPO is the inverse of sum-frequency generation processes like second harmonic generation. In OPO conversion, two variable frequencies, related as follows:

$$\frac{1}{\lambda_p} = \frac{1}{\lambda_1} + \frac{1}{\lambda_2},$$

where $\lambda_p$ is the pump wavelength, are determined by the particular phase matching used. Only one pair of frequencies can be phase matched at a time. By adjusting the phase matching parameters, e.g., the temperature or orientation of the non-linear crystal in an OPO setup, the output can be "tuned" over a range of frequencies. In OPO arrangements, the pump wavelength is always converted into two longer wavelength components, $\lambda_1$ and $\lambda_2$.

Other efforts have been directed to providing laser light at a single optimal wavelength which could provide satisfactory cutting and coagulative abilities. In fact, the development of the Ho:YAG laser with its 2.1 micron output is understood to have been the result of just such a study. No such optimal single wavelength has been identified, however, as results generally show inferior cutting and inferior sealing.

It has been speculated that a compound laser system capable of producing the cleanness of incision of a CO$_2$ laser or an Er:YAG laser, along with the photocoagulative ability and hemostatic control of, for example, a Nd:YAG laser would be a valuable surgical tool. As set forth in his article titled "Laser Surgery: CO$_2$ or HF", Myron L. Wolbarsht (IEEE J. Quantum Electronics, QE-20, No. 12, December, 1984), such a compound laser system was envisioned as literally incorporating several laser types available for simultaneous use. Wolbarsht specifically suggested the use of HF laser technology for optimum cutting, and an argon-ion or Nd:YAG laser for deeper penetration and increased coagulation. As set forth above, the size and toxic nature of the gas of the HF device makes it a poor choice for use in surgical applications, and the combination of two expensive laser devices would not only be cost prohibitive, but would also be difficult to structurally arrange for is convenient and accurate use. Moreover, the development of fiber optic delivery systems for the CO$_2$ wavelength laser continues to lag far behind those for other medically useful wavelengths such as the 1.064 micron YAG laser. In any event, no such device has been made available in the industry.

U.S. Pat. No. 4,791,927 which issued to Menger allegedly provides a laser scalpel which can cut tissue with a wavelength in the near UV range, while a second wavelength in the 600–700 nm range cauterizes the tissue. However, the substantially red light (600–700 nm) is ill-suited for coagulation of oxygenated hemoglobin (which reflects red light), and light in the near UV range is not particularly useable for cutting or coagulating due to interference caused by high absorption of these wavelengths by other elements of tissue such a melanin and DNA, which can cause an increased risk of carcinogenesis.

Consequently, heretofore there has not been provided a single practical device for delivering a single laser light beam having two or more medically useable wavelengths which could, for example, optimize simultaneous cutting and sealing in a single operation. Moreover, there has not been available a metal vapor laser which can simultaneously develop two medically desirable wavelengths (such as 1.13 microns and 2.55 microns) for instantaneously and optimally producing medically desired results, such as superior incisions and optimum coagulative ability, with a single tool.

DISCLOSURE OF THE INVENTION

It is an object of this invention to obviate the above-described problems and shortcomings of the laser devices heretofore available in the industry.

It is another object of the present invention to enable a metal vapor laser device to develop two medically usable light beam wavelengths simultaneously for use in various medical applications.

It is also an object of the present invention to provide a laser system which can develop a laser radiation output having two predetermined wavelengths which are provided coaxially and are endoscopically compatible.

It is yet another object of the present invention to provide a metal vapor laser system which can produce a coaxial laser light beam having a predetermined and controllable mix of two or more wavelengths from a single laser source for simultaneous use in medical applications.

In accordance with one aspect of the present invention, there is provided a laser system having an active laser gain medium comprising metal vapor which, when excited, produces laser radiation at a plurality of medically useable wavelengths. A plurality of medically useable wavelengths are coaxially transmitted from the laser system for simultaneous use in a medical procedure. One of the wavelengths transmitted is closely matched to a light absorption peak of either water or Hemoglobin, and another wavelength is matched to the other of these light absorption peaks. The disclosed laser system can also include a laser gain medium comprising a plurality of metal vapors to produce the plurality of wavelengths desired. In preferred embodiments, the metal vapors can include barium, thulium, and/or samarium. Additional laser conversion equipment can be included to convert at least a portion of the laser radiation produced by the gain medium to one or more additional medically useable wavelengths for coaxial transmission.

BRIEF DESCRIPTION OF THE DRAWINGS

While the specification concludes with claims particularly pointing and distinctly claiming the present invention, it is believed the same will be better understood from the following description taken in conjunction with the accompanying drawings in which:

FIG. 2 is a graphical representation of the relative absorption of light radiation by oxygenated and deoxygenated Hemoglobin at various wavelengths (microns) on the spectrum;

FIG. 3 is a schematic diagram embodying a conversion system made in accordance with the subject invention;

FIG. 5 is a schematic illustration of a typical application of the subject conversion system in connection with a medical laser system;

DETAILED DESCRIPTION OF THE INVENTION

Figure 1:
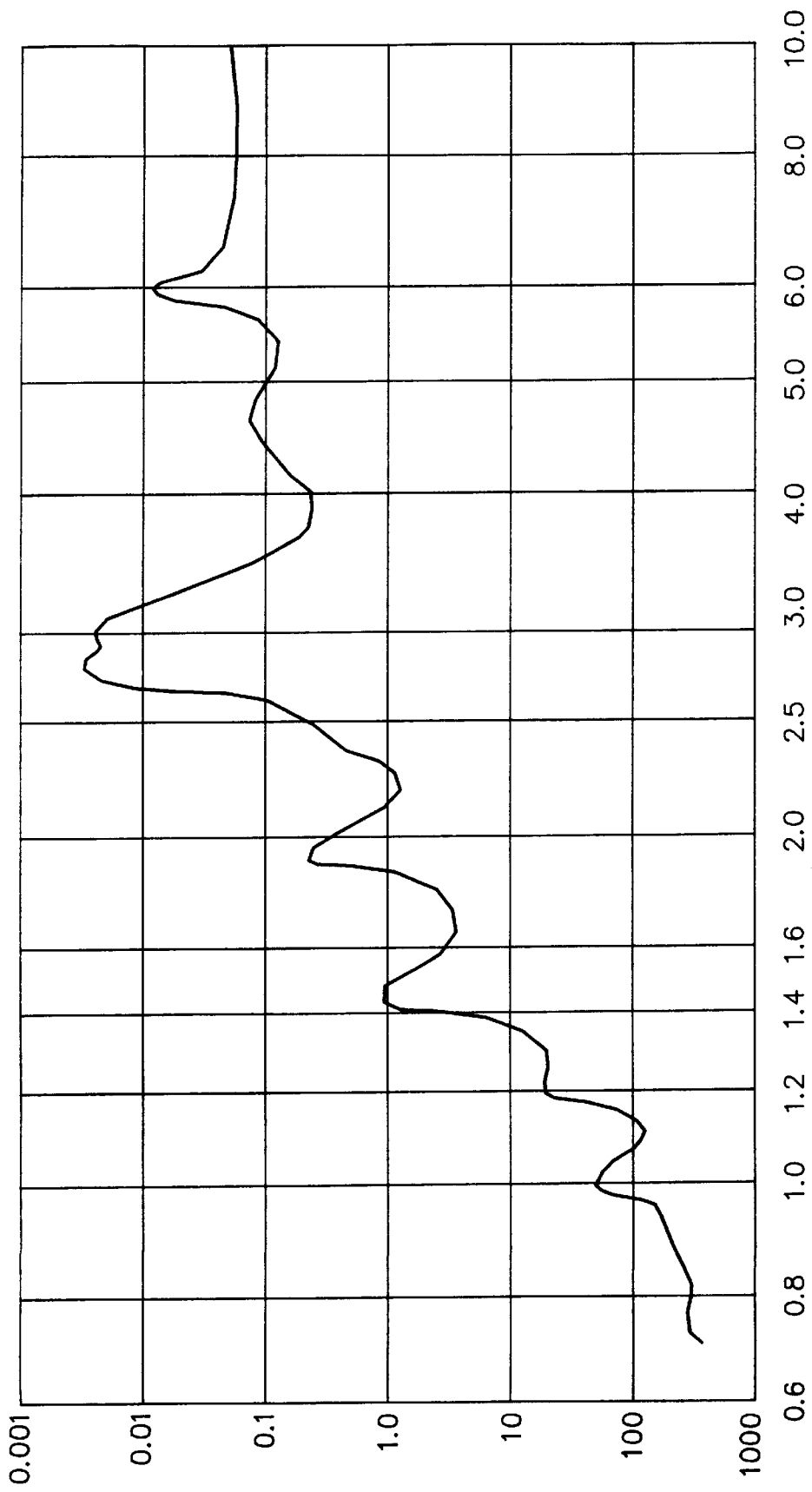
FIG. 1 is a graphical representation of the relationship between water absorption of light radiation (extinction length in mm) at various wavelengths (microns) on the spectrum.

Referring now to the drawings in detail, wherein like numerals indicate the same elements throughout the views, and wherein numerals having identical last two elements (e.g. 17, 117, 217) indicate corresponding structures between the various embodiments, FIG. 1 is a graphical representation of the relative absorption levels of light radiation (i.e. the extinction length for diminishing the intensity of entering light down to $e^{-1}$) by water at various wavelengths.

As mentioned, because tissue is approximately 80% water, the coefficient of absorption of light energy by water will determine the characteristics of laser interaction in tissue. In order to optimize the efficiency of, for example, cutting or heating of tissue, and to minimize unnecessary tissue damage (such as by thermal damage), an output wavelength closely matched to a water absorption peak should be utilized. FIG. 1 shows that a water absorption peak occurs approximately at a wavelength of between about 2.85 to 2.95 microns, and more generally between about 2.7 and 3.25 microns.

Consequently, the Er:YAG laser is of special interest, since it has an output of approximately 2.9 microns which closely coincides with a water absorption peak. Assuming equal (i.e. time and size) application of laser radiation produced by the Er:YAG at 2.9 microns and radiation produced by a $CO_2$ laser at an output wavelength of 10.6 microns, the thickness of soft tissue damage beneath the excision made by the Er:YAG laser will be much less and preferred over the $CO_2$ laser. However, high quality, reliable pulsing technology is not available for the Er:YAG systems, as the rotating mirror Q-switching technology available is relatively unreliable and inferior to the electro-optic Q-switch technology, such as is available for Nd:YAG systems. The rotating mirror is subject to mirror instability or "wabble", which can cause variance in the beam divergence, spatial profile, and spatial stability. The inconsistency of the resulting radiation energy make this technology unsatisfactory for most micro-surgical procedures.

To respond to these problems, frequency doubling techniques such as optical parametric oscillators or Raman shifting devices have been utilized to convert light beams at longer wavelengths (e.g. 10.6 micron and 1.064 microns) to shorter wavelengths (e.g. 2.9 microns and 0.532 microns) to provide light radiation at a water absorption peak or in the visible light spectrum. Frequency doubling, however, drastically reduces the power output as a result of the relatively low (e.g. about 70% or less) efficiency of such techniques, in addition to the lack of technology for providing pulsed application of radiation from $CO_2$, Er:YAG and Ho:YAG lasers in order to limit unnecessary thermal damage of the tissue.

FIG. 2 illustrates a graph similar to that of FIG. 1, plotting the relative absorption (vertical axis) of light by oxygenated ($HbO_2$) and deoxygenated (Hb) Hemoglobin (i.e. blood) for various wavelengths (horizontal axis). Since the pertinent absorption peaks for both oxygenated and deoxygenated Hemoglobin are substantially the same, for the purposes of this discussion, both will be jointly considered generally as Hemoglobin. As can be observed, an absorption peak for Hemoglobin occurs within an approximate range of wavelengths between about 0.5 and 0.6 microns. While higher peaks of absorption are present at shorter wavelengths, the peaks at wavelengths less than 0.5 microns are not preferred due to interfering effects of inordinant absorption of shorter wavelength radiation by other aspects of the tissue (e.g. Melanin exhibits enormous absorption of radiation at about 0.4 microns). Radiation in a range of between about 0.5 and 0.6 microns is preferred as it is more transparent to extraneous absorbers such as Melanin. As a consequence, laser radiation in this approximate range provides the most efficient hemostasis control by heating the adjacent blood vessels and augmenting coagulative abilities of the laser tool.

Frequency doubling of the output of an Nd:YAG laser (1.064 microns) can produce radiation at a wavelength of approximately 0.532 microns, which provides very good coagulative abilities. Similarly, a non-solid state dye type laser can produce a light beam having a wavelength of approximately 0.577 microns. An advantage of working with laser light in the visible spectrum (e.g. 0.532 microns or 0.577 microns) is that the beam itself can be seen and there is no need for the use of an additional beam such as a HeNe (Helium Neon) beam to provide visible indication of the light path to assist the surgeon.

Consequently, while devices are available in the industry to provide laser light at the respective absorption peaks for water and for hemoglobin, heretofore each device was particularly designed to provide concentrated laser light output at only a single wavelength. A tradeoff was often required between provision of light radiation at a wavelength which, for example, could provide optimal cutting abilities, and a wavelength which would provide improved coagulative abilities and hemostasis. In fact, foresighted experts in this field specifically envisioned the future incorporation of several lasers for simultaneous use.

A compound laser system capable of producing a clean incision along with photocoagulative ability and hemostatic control was contemplated as physically incorporating one laser source for cutting (e.g. a CO2 laser or an HF laser), and another shorter wavelength laser source (e.g. the Nd:YAG or argon-ion laser) for hemostatic control. However, the slow development of fiber optic delivery systems for the $CO_2$ wavelength lasers, and the impracticality and inadvisability of utilizing the HF laser in an operating room environment have no doubt been factors in preventing such a compound laser from becoming a reality.

The present invention provides a single, solid-state laser conversion system and method for outputting a plurality of predetermined wavelengths (e.g. one wavelength for optional cutting and another for optimal hemostasis) simultaneously and coaxially for convenient use by the surgeon. The multi-wavelength output is a single light beam which can be conveniently focused and directed onto a single target or treatment area for simultaneous application. FIG. 3 illustrates a schematic diagram of a conversion system 10 made in accordance with the subject invention. Conversion system 10 is designed for convenient use with an existing laser system commonly available in the industry, and is contemplated as a relatively low-priced accessory which can be added to a laser system already available in a hospital, clinic, or the like. Such arrangement is seen as providing a low cost way of adapting existing equipment and commercially available laser devices in order to optimize the effectiveness thereof for particular procedures, and to enable application of those devices to a relatively unlimited array of additional medical and surgical procedures.

Conversion system 10 is illustrated as including a focusing device 15 for focusing laser radiation at a predetermined pump wavelength 24 into a conversion medium 40 located within conversion cavity 30. Focusing device 15 can conveniently comprise a beam expander 17 and a collimating lens 19 to focus a laser radiation source beam 22 provided by laser 20 to a predetermined diameter D. Diameter D is determined to appropriately correspond with the cross-sectional area of conversion medium 40, such that the beam 24 of coherent light at a predetermined pump wavelength will be focused to occupy the optimum volume of conversion medium 40 without resulting in undesirable diffraction effects. Focusing device 15 can also preferably provide means for varying the size and direction of pump beam 24 to enable conversion system 10 to be adaptable to a variety of conversion media 40, and to facilitate the adaption of system 10 to provide a variety of predetermined wavelengths, as desired.

Conversion cavity 30 further includes a first window or entrance 32 for receiving laser radiation at a predetermined pump wavelength. While pump wavelength 24 may be identical to the wavelength of source beam 22, it is contemplated that the wavelength of source beam 22 might also be altered (e.g. by frequency doubling from 1.064 microns to 0.532 microns) prior to being focused into conversion cavity 30. First window 32 preferably includes an outer surface 34 treated, coated or otherwise structurally adapted to reduce or eliminate reflection of incident laser radiation at the predetermined pump wavelength, and an inner surface 36 similarly adapted for high transmission of laser radiation at the predetermined pump wavelength and for high reflectivity of the conversion or signal wavelength. Light beam 24 enters conversion cavity 30 and medium 40 for conversion to a signal wavelength in a range of between about 2.7 and 3.25 microns.

Conversion medium 40 can be any structure capable of relatively efficient conversion of a portion of radiation at a predetermined pump wavelength to a predetermined signal wavelength. For example, a pump wavelength of 0.532 microns (a wavelength preferred for good hemostatic control) might be provided, and a portion of the radiation would be converted to a wavelength in a range of between about 2.7 and 3.25 microns (a range preferred for optimal cutting), or vice versa. Because the pump wavelength is preferably predetermined to be medically useable (as used herein the term medically useable shall be understood to mean a wavelength beneficial or desirable for a particular procedure such as cutting, diagnosing, heating, coagulating, or otherwise treating), the output beam is to include a predetermined percentage of radiation at the pump wavelength, and total conversion of the pump wavelength is obviously undesirable. It is preferred that medium 40 comprise an optically non-linear crystal such as the commonly available KTP (as available from Airtron Company in the United States, and FIMS and Shandong University in China).

Conversion medium 40 can also be provided as a Raman cell which, through Raman shifting, can partially convert radiation at a predetermined pump wavelength (e.g. 1.064 or 0.532 microns) to the desired signal range (e.g. between about 2.7 and 3.25 microns). Because the Raman cell will include a gaseous conversion medium (e.g. methane), the light radiation photons will pass through a conversion medium having a much lower density than the KTP material used in the optical parametric oscillator alternative, and the length of conversion medium 40 will necessarily be much longer. The practical difficulties with the Raman approach may indeed make it much less desirable for use as conversion medium 40 than OPO crystals such as KTP, beta-barium-borate (BBO), LAP, $KNbO_3$, or urea. It should also be noted that the conversion medium of the present invention may comprise a plurality of structures such as one or more crystals and/or Raman cells in combination to convert portions of a pump wavelength from a single radiation source into a plurality of medically useable wavelengths as desired.

First window 32 is located at the entrance or proximal end of conversion cavity 30, and a second or transmission window 50 is spaced from window 32 along the longitudinal axis A of cavity 30 and located adjacent the proximal end thereof. Windows 32 and 50 may preferably be formed of material such as calcium fluoride ($CaF_2$). While the conversion efficiency of a conversion crystal such as KTP or BBO generally increases with increased crystal length, it is often desirable to minimize the overall length of an OPO cavity such as conversion cavity 30 for practical application and convenience of the user. In order to provide a conversion cavity with reduced length, it will often be desirable to design the conversion system for ensuring multiple passes of light from laser beam 24 through conversion medium 40 within conversion cavity 30.

In order to provide multiple passes of the light beam through conversion medium 40, second window 50 preferably includes an inner surface 52 prepared for limited transmission (e.g. 20% to 35%) of light at the conversion or signal wavelength (e.g. in a range of between 2.7 and 3.25 microns), and which will be at least partially resonant of radiation at the predetermined pump wavelength (e.g. 1.064 microns). It is important that the inner surface 52 of second window 50 and inner surface 36 of first window 32 provide sufficient resonance of radiation at the predetermined pump wavelength to enable relative efficient conversion of a portion of that pump wavelength radiation to the desired signal wavelength.

Additionally, transmission window 50 has an outer surface 54 which is preferably anti-reflective at the signal wavelength to facilitate transmission of radiation within the desired signal wavelength range from conversion system 10 for use. Consequently, on average, first window 32 and second window 50 provide for limited resonance of light at the predetermined pump wavelength within conversion cavity 30 such that it makes several passes (e.g. 5) through conversion medium 40 before being transmitted through second window 50 for use.

While it is generally desirable to keep the length of conversion cavity 30 to a minimum, the length of this cavity and the average number of passes through conversion medium 40 of light at the pump wavelength will be constrained by the Raleigh length which is related to the diameter of the beam and the wavelength itself. In particular, the Raleigh length is that length at which the light beam begins to spread significantly and the intensity of the light begins to appreciably degrade. The Raleigh length can be determined as follows:

$$\text{Raleigh length} = \frac{\pi W_o}{\lambda}2$$

Where: $W_o$=radius of light beam $\lambda$=wavelength of pump beam

As it is understood that the energy of the light beam 24 passing through conversion medium 40 must be focused sufficiently to exceed the threshold level of a particular crystal (e.g. KTP, BBO LiIO$_3$, KNbO$_3$, or BNN), it is important that the length of conversion cavity 30 and the average number of passes of the light radiation within conversion cavity 30 are sufficient to ensure that the light beam remains relatively focused and that the threshold level of energy is maintained for optimum efficiency of conversion. It is important to fill the volume of the conversion medium (e.g. a KTP crystal) as uniformly as possible over its entire length while maintaining the relatively high intensity required for efficient OPO conversion.

It is also important that the light beam diameter be small enough relative to the effective "diameter" of conversion medium to minimize effects of diffraction. The elements of focusing device 15 must be properly chosen to expand and collimate the pump light beam 24 so that the light can traverse conversion cavity 30 many times before the diffractive spreading becomes large enough to interfere with the OPO conversion.

As an example, where the total length of conversion system 10, including conversion cavity 30 and focusing device 15, is to be approximately 6 inches (approximately 15.3 cm) for conversion of an Nd:YAG laser providing a source beam 22 and pump beam 24 having a wavelength of 1.064 microns, a KTP crystal with a cross-sectional dimension of 3 mm×3 mm may be used, and a beam spot size ($W_o$) having a radius of 0.5 mm provided with an on-axis intensity within the KTP crystal of approximately 100 MW/cm$^2$, and with a depth of focus of focusing device 15 at 21 cm. The 0.5 mm radius of pump beam 24 is small enough to obtain the high intensity required for efficient OPO conversion, but is large enough to yield long depth of focus (i.e. the distance the beam travels without appreciable diffraction) and to avoid crystal damage. KTP has a damage threshold (D.T.) of approximately 0.4 GW/cm$^2$ for a 10 ns pulse at 1.064 microns. Consequently, the 100 MW/cm$^2$ intensity is well below the damage threshold for this crystal. BBO has an even higher damage threshold of 5 GW/cm$^2$.

First window 32 and second window 50 are provided to increase the overall conversion efficiency of cavity 30 by reducing the reflection loss experienced by the pump light beam at the cavity input, by increasing the average interaction length of the pump light beam with the conversion medium 40, and by increasing the percentage of the conversion or signal wavelength light exiting the cavity's output or distal end. It is also contemplated that the individual elements of focusing device 15 will be provided with anti-reflective surfaces as well to minimize reflection loss. Light exiting the distal end of conversion cavity 30 (i.e. the output of conversion system 10) comprises a coaxial (e.g. along axis A), multi-wavelength output beam O including the predetermined pump and signal wavelengths.

For example, where a pump wavelength of 1.064 microns from an Nd:YAG laser is utilized, a portion of the pump beam wavelength will be downshifted to approximately 2.9 microns by conversion medium 40 (e.g. KTP crystal), and the output O will comprise a light beam having wavelengths of 1.064 and 2.9 microns. Such dual wavelength output can provide clean cuts as a result of its 2.9 micron wavelength, with simultaneous focused and instantaneous coagulative abilities as a result of the shorter 1.064 micron wavelength. The coaxial, single beam compound wavelength output of the present invention obviates a need for aligning separate laser beams from multiple sources, as the output is precisely focused at the target or spot of treatment by the operator.

As indicated above, source beam 22 from an Nd:YAG laser at 1.064 micron wavelength could be frequency doubled prior to its introduction to conversion system 10 such that pump wavelength 24 would be 0.532 microns, and the resulting multi-wavelength output O would comprise light at both the pump wavelength of 0.532 microns and the signal wavelength of 2.9 microns. While frequency doubling of the source beam 22 would tend to reduce the power of pump wavelength 24 and the resulting 0.532 micron portion of output O, it is believed that the power levels obtainable for both wavelengths will be sufficient to provide clean cuts and instantaneous and focused hemostasis control with the use of a single Nd:YAG laser source.

OPO conversion uses a non-linear crystal to convert light at a pump wavelength into two longer output wavelengths, the signal and the difference frequency or idler frequency. For example, if the signal wavelength is chosen (i.e. by selection of the conversion medium) to lie in the 2.7–3.25 micron range, and the pump wavelength lies between about 0.532 and 1.318 microns, the resulting idler wavelength will always take on a value greater than the pump wavelength but less than that of the signal. Particularly, the idler frequency wavelength is equal to the difference between the signal and pump wavelengths. Therefore, the hemostasis produced by the idler wavelength will be less than that produced by the pump wavelength, and the cutting ability of the idler frequency will be less than that of the signal. In most cases, the idler component of the output does little to enhance the medical efficacy of the system and can be ignored.

There can be applications, however, where the idler or difference frequency may fall within a wavelength range which can indeed add to the effectiveness of the coaxial pump or signal wavelength of the output O of the present invention. One such exception occurs when the pump wavelength is chosen to be 0.532 microns and the idler frequency is approximately 0.583 microns, resulting in a signal output wavelength of about 6.1 microns. Although the 6.1 micron wavelength is not absorbed as strongly by water as the preferred 2.7–3.25 micron wavelength, it is more strongly absorbed than the above-described 10.6 micron $CO_2$ laser output. Additionally the idler wavelength is near the Hemoglobin absorption peaks, thus increasing the hemostasis potential of the system. Consequently, both the idler and pump frequencies would provide medically useable radiation for enhancing hemostatic control, while the signal wavelength is medically useable to simultaneously provide efficient cutting abilities.

Although the relative merits of various candidate wavelength sets must be determined by in vivo testing, this particular combination of wavelengths may represent a preferred choice for many applications. Unfortunately, although the non-linear crystal is available for producing this particular output wavelength set (e.g. $LiNO_3$, $KNbO3$ or BNN), optical fibers capable of transmitting the 6.1 micron wavelength with low energy loss are only currently being developed. Consequently, optimal implementation of the full variety of applications for the present invention may be delayed until corresponding related technology (e.g. fiber-optics) is available.

It has been found that the optimum conversion utilizing OPO technology occurs when there is an approximate 2:1 ratio between the desired signal or conversion wavelength (e.g. 2.7–3.25 microns) and the pump wavelength (e.g. 1.064). For this reason, because conversion of the 1.064 micron wavelength to an approximate 2.9 micron wavelength is further from the desired ratio (i.e. 1:2) than would be conversion from a modified 1.318 micron Nd:YAG laser pump wavelength to approximately 2.9 microns, it may well be preferred to modify the Nd:YAG laser to provide the 1.318 micron wavelength (i.e. by changing the YAG lasers reflecting mirrors as appropriate).

On the other hand, while conversion of the frequency doubled Nd:YAG source beam of 0.532 microns to approximately 2.94 microns (signal wavelength) may result in some energy being wasted due to the inefficiencies of conversion (i.e. not a 1:2 conversion), an optimal pair of cut/seal radiation wavelengths may be obtained in this way. It should be noted that upshift conversion (such as by frequency doubling) of a pump wavelength in a range of between about 2.7 and about 3.25 microns to a signal wavelength in a range of between about 0.5 and about 1.2 microns could equally be effected by the present invention to provide two similarly useful wavelengths simultaneously.

Figure 4:
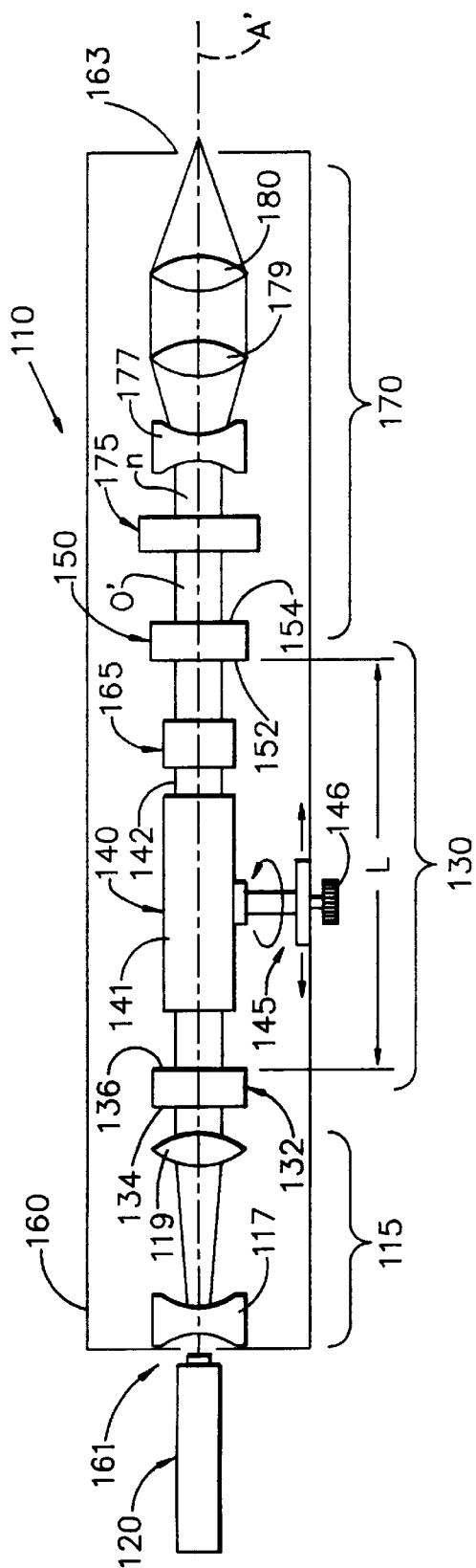
FIG. 4 is a schematic diagram of a laser system embodying a preferred application of the conversion system of the present invention.

FIG. 4 illustrates a conversion system 110 utilized with a laser 120 in a preferred arrangement. In particular, conversion system 110 is shown as being substantially enclosed within a housing 160 having a receiving means or input opening 161 at its proximal end, and a transmission means or output opening 163 at its distal end. Within housing 160 is located focusing device 115 which can similarly include a beam expander 117 and a collimating lens 119. Conversion cavity 130 is shown as including first window 132, conversion medium 140 (preferably comprising an OPO crystal 141), and a second window 150 similar to the corresponding structure described above with regard to conversion cavity 30. Length L of conversion cavity 130 will similarly be determined in accordance with the discussion above and the Raleigh length limitations.

An adjustment device 145, such as a microlinear/rotary stage, is optionally provided to enable tuning of the conversion medium by adjusting its orientation and/or axial position, such as via adjustment knob 146. Phase matching of the non-linear crystal in OPO applications, such as shown and described in U.S. Pat. Nos. 4,639,923 (Tang et al.) and 4,180,751 (Ammann), can be accomplished by adjusting the crystal orientation to "tune" the output wavelengths within a certain range, as desired.

Preferably included within conversion system 110 is a Q-switching device 165 for providing optimal control of the temporal pulse width and size of the dual wavelength output of conversion system 110. Various acoustic-optical and electro-optical Q-switching technology is available in the industry, such as described in U.S. Pat. No. 4,455,657, and will not be discussed in detail herein. Generally, the Q-switch device 165 is utilized as a means for deflecting light photons within conversion cavity 130 to diffuse power from the central axis on an intermittent basis such that concentrated short bursts of dual wavelength laser energy can be provided by conversion system 110 for use in various medical applications. As mentioned, reduction of the temporal length of successive bursts of light energy can correspondingly reduce the size of the zone of thermal damage in laser surgery.

Multi-wavelength light energy O' is produced along axis A' in a manner corresponding with that described above with regard to FIG. 3, and is passed through an optional selective wavelength controller 175, which can comprise a variable filter or, in some cases, a beam splitter. In particular, it is contemplated that in many applications it may be preferred to obtain a predetermined mixture of the several desired wavelengths for very specialized applications. For example, hemostatic control in highly perfused tissue may require a higher concentration of output light in the shorter wavelength zone (i.e., the high blood absorption wavelength), wherein it is preferred to throttle back the percentage of transmitted light at the higher wavelengths (i.e., the output light in the 2.7 to 3.2 micron range). Consequently, while the present invention provides the unique ability to produce a multi-wavelength, coaxial light beam comprising a predetermined mixture of two or more simultaneously applicable wavelengths (e.g. for cutting and instantaneously sealing blood vessels and the like), it further provides an advantageous adaptability of custom mixing the output wavelengths.

As an example, some surgical procedures involve tissue which is relatively bloodless, wherein the shorter wavelength light for coagulative action is not needed. In such a situation, selective wavelength controller 175 could reduce or eliminate the low-water absorption wavelength. In such instances, the output beam O' could be adjusted to a modified output beam M.

Whether or not the output of conversion system 110 is modified by a selective wavelength controller 175, the output of system 110 will preferably be appropriately focused for delivery to a laser tool or the like, such as by beam expander 177, collimator lens 179 and focusing lens 180, as illustrated in FIG. 4.

FIG. 5 illustrates a typical application of the subject conversion system in connection with a laser system 20, such as an Nd:YAG laser arrangement often found in hospitals, clinics and the like. Laser system 20 is shown as including a cooling apparatus 126 such as a water cooling setup, and a source beam delivery apparatus 28, such as a fiber-optic cable. As illustrated, solid-state conversion system 110 would preferably be located adjacent to laser system 20 to receive the source beam via delivery apparatus 28 at input opening 161. Within housing 160 would be located all of the necessary conversion elements as described above with respect to FIG. 4, and the multi-wavelength, coaxial output beam O' (or the modified output beam M) would be transmitted from conversion system 110 through output opening 163.

A set of lenses such as described above with regard to beam expander 177, lens 179 and focusing lens 180 would preferably provide for efficient coupling of the multi-wavelength output beam into an optical fiber cable 185 for convenient transmission to a remote laser tool 190. As described above, conversion system 110 can be specifically set up and adapted to work in conjunction with a variety of solid-state and dye laser devices currently available in the industry such as the Nd:YAG laser. By a combination of manipulation of the source beam (e.g. frequency doubling) and appropriate adaption of the conversion cavity of conversion system 110, a predetermined pair of wavelengths comprising one wavelength in a range of between about 2.7 and 2.9 microns (i.e., a wavelength near the absorption peak of water) and a second shorter wavelength near the absorption peak of Hemoglobin is produced in a preferred embodiment.

Figure 6:
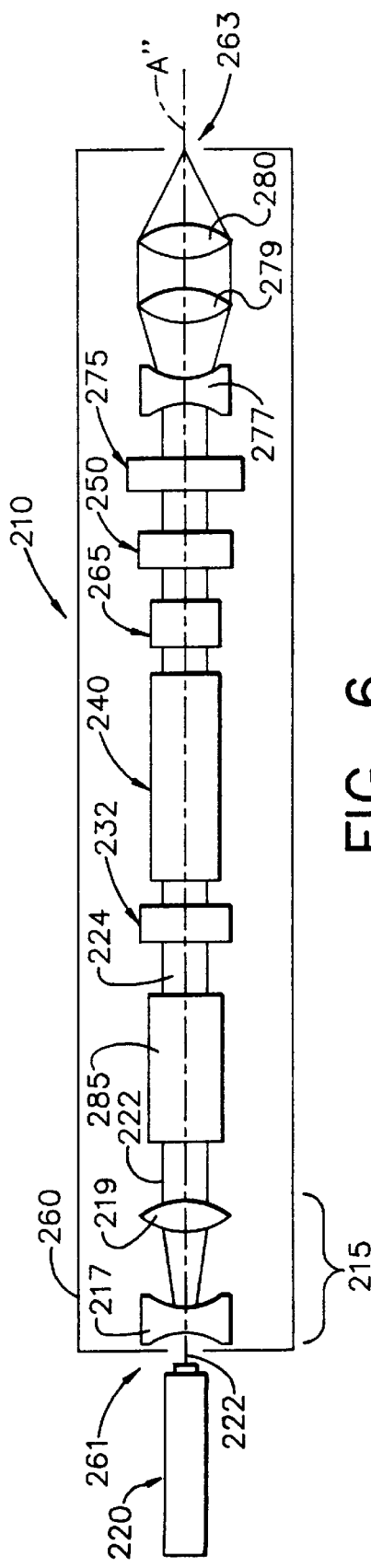
FIG. 6 is a schematic illustration of an alternate embodiment of the subject conversion system.

FIG. 6 schematically illustrates yet another alternate embodiment of a conversion system 210 made in accordance with the subject invention, including elements corresponding to each of the elements described above with regard to FIG. 4, with the addition of an optical frequency doubler or frequency doubling device 285 to modify the source beam 222 to a predetermined pump wavelength beam 224. It is contemplated that it will be preferred to focus source beam 222 (such as via focusing device 215) prior to its introduction into frequency doubling device 285, as illustrated. An arrangement as shown in FIG. 6 could be utilized to convert the source beam 222 from an Nd:YAG laser 220 at a wavelength of 1.064 microns into a pump beam 224 having a wavelength of 0.532 microns, as mentioned above.

The balance of conversion system 210 would preferably include corresponding structure and operate as described above with regard to the embodiment 110 of FIG. 4. As in the other embodiments, the multi-wavelength output light beam, having a combination of wavelengths such as 0.532/2.9 microns, 1.32/2.9 microns, 1.064/2.9 microns, 0.532/6.1 (with 0.583 idler) microns, or 0.532/2.3 (with 0.630–0.690 idler) microns, will be provided through output opening 263, which can be directly coupled to an optical fiber (e.g. 185) for delivering the multi-wavelength output to the target for simultaneous use.

It is further contemplated that the receiving means or input opening (e.g. 61, 161, 162) of the subject conversion system can also be fitted with fiber-optic or mechanical attachment means for facilitating relatively quick attachment of the conversion system to existing Nd:YAG or KTP medical laser systems commonly used in the industry. As such, the multi-functional conversion system can provide a valuable aftermarket or add-on device capable of enhancing and expanding the useful application of any particular laser system.

The solid-state conversion system of the present invention will preferably be assembled and designed for use with a particular laser device to provide a coaxial light beam output having a predetermined plurality of medically useable wavelengths chosen to provide, for example, both superior cutting and coagulative abilities simultaneously. In this way, precise assembly and adjustment of the conversion medium (such as an OPO crystal) can be accomplished in the factory. Because the angle of cut and the angle of orientation of any particular OPO crystal is quite important in providing an OPO resonant cavity and conversion assembly, precise orientation of the crystal can be accomplished during assembly by utilization of an adjustable mount or mounting device (e.g. a microlinear/rotary stage device 145 or similar precision stage positioner) so that the conversion system can be tested and appropriately adjusted prior to completion of the assembly process. As indicated, means for adjusting the crystal position and orientation can equally be provided as part of the conversion system itself to allow for field tuning as well.

The subject conversion system results in the unique provision of a single output beam which can, in a preferred example, include a predetermined mixture of light energy at a first wavelength that is much more strongly absorbed by water, and at a second wavelength which is much more strongly absorbed by blood, at a common tip for simultaneous use. This unique combination of radiation wavelengths can provide optimized tissue cutting abilities with instantaneous coagulative capabilities, resulting in cleaner, faster, safer and essentially "ubloodless" surgical procedures.

Some power will inevitably be absorbed and converted into heat within the conversion system, however, such heat within the various components is small enough such that the conversion system can generally be operated without a need for additional means for cooling. It is contemplated that a relatively thin but protective housing (e.g. 60, 160, 260) may be utilized which itself can facilitate cooling of the system by natural convection/heat exchange processes. While additional cooling structure is not believed necessary, the addition of such could be simply accomplished if desired by a variety of means available to those or ordinary skill.

The present invention can similarly be used for other medical treatment and/or diagnostic purposes. For example, photodynamic therapy (PDT) utilizes relatively low intensities of laser light, in combination with a photosensitizing agent such as hematoporphryin derivative ($H_pD$) to disrupt the vasculature of tumors. Typically, PDT involves application of light in the range of between about 0.630 and about 0.690 microns which is absorbed by the photosensitive material to effectively destroy the tumor. It has been determined that, in many cases, PDT is enhanced by hyperthermia.

Some researchers have utilized two separate lasers, one emitting light at 0.630 microns and the other a Nd:YAG laser operating at 1.064 microns, in order to combine the PDT and hyperthermia treatments. The present invention can accomplish both simultaneously with a single laser by (for example) first frequency-doubling a 1.064 micron laser beam to 0.532 microns, then providing a conversion medium to provide an idler frequency in a range of between about 0.630 and about 0.690 microns (depending upon the particular photosensitizing agent used), as well as light at a signal wavelength in the 2.3 to 3.4 micron range. The infrared light is suitable to induce hyperthermia as it is more strongly absorbed by the water content.

In this fashion, a single laser can be used for the combined instantaneous treatment, eliminating the difficulties of alignment of two separate beams and the extra cost associated with two lasers. The combined treatment is precise because the various wavelengths are simultaneously applied to the exact treatment area or target. Additionally, the laser devices currently used to provide light at 0.630–0.690 microns is an Argon-dye laser, which is very large and unwieldy to work with because of the laborious dye changing requirements. The present conversion system obviates these problems, and enables use of commonly available 1.064 Nd:YAG devices. It is believed that there are numerous other procedures which require a plurality of treatments which could be simultaneously provided from a single laser source via the subject conversion system and method in similar fashion.

As mentioned, a selective wavelength controller (e.g. 175) can be utilized to remove some percentage of the pump wavelength from the output beam, such as to provide a relatively higher concentration of one or more of the outer wavelengths as desired. For example, depending upon the type of target tissue (e.g. corneal, cartilage, skin, muscle, organ, etc.), the surgeon may choose to reduce some portion of the wavelength(s) which will be generally more strongly absorbed by blood. Tissue prone to greater blood loss will require a higher percentage of the wavelength in the shorter range (e.g. 0.5–1.2 microns) than tissue such as cartilage or corneal tissue. In surgical procedures on corneal tissue, it may be preferred to completely eliminate the shorter wavelength, as such surgery is essentially bloodless. A single conversion system made in accordance with the subject invention can be fitted with replaceable or variable filtering lenses to allow a wide variety of mixtures of the resulting wavelengths for all of these applications.

In particular arrangements, it may be preferred to attach first window 32 and second window 50 immediately adjacent to the proximal and distal ends of conversion medium 40. This could also be accomplished by direct application of an appropriate coating surface to each of the proximal and distal ends of conversion medium 40 to eliminate a need for independent optical devices, to minimize the overall length of conversion cavity 30, or to eliminate unnecessary interfaces between optical components and various air spaces. As indicated, the variety of applications for converting a single wavelength laser beam into a beam including two or more medically useable wavelengths for simultaneous, coaxial use is virtually unlimited.

The present invention can be utilized for other therapeutic applications, such as tissue welding. U.S. Pat. No. 4,672,969 discusses the use of infrared light to denature tissue under irradiation, forming a biological "glue" which welds the tissue. If the wavelength is too strongly absorbed by the tissue, the weld strength can suffer. Likewise if the wavelength penetrates too deeply into the tissue, either too much tissue is heated to coagulation, or not enough energy is absorbed at the target to create the "glue". Clinical research has indicated that unless exogenous chromophores are added, light in the very near IR range (e.g. 750–950 nm) penetrates too deeply. For example, light with greater tissue absorption than the light from the $CO_2$ laser (10.6 microns) is too strongly absorbed.

A non-thermal physical mechanism which can be utilized to "weld" biological tissue involves irradiation of targeted tissue with laser light while heating of the tissue is controlled, such as by use of saline solution or similar fluid. The tissue temperature is controlled to such an extent that thermal denaturation of the collagen is not possible, and the "welding" that results is believed to result from a photochemical process. The laser most frequently used for this procedure is the argon-ion laser emitting radiation at 514.5 nm.

The present invention can be utilized to provide simultaneous laser outputs suitable for either the thermal or photochemical-based welding approaches. For example, a laser including copper vapor with output at about 511 nm, and thulium vapor with output at about 1.68 microns can achieve both required wavelengths, as could a combination of copper vapor and barium vapor (with output at 1.13 and 1.5 microns).

Figure 7:
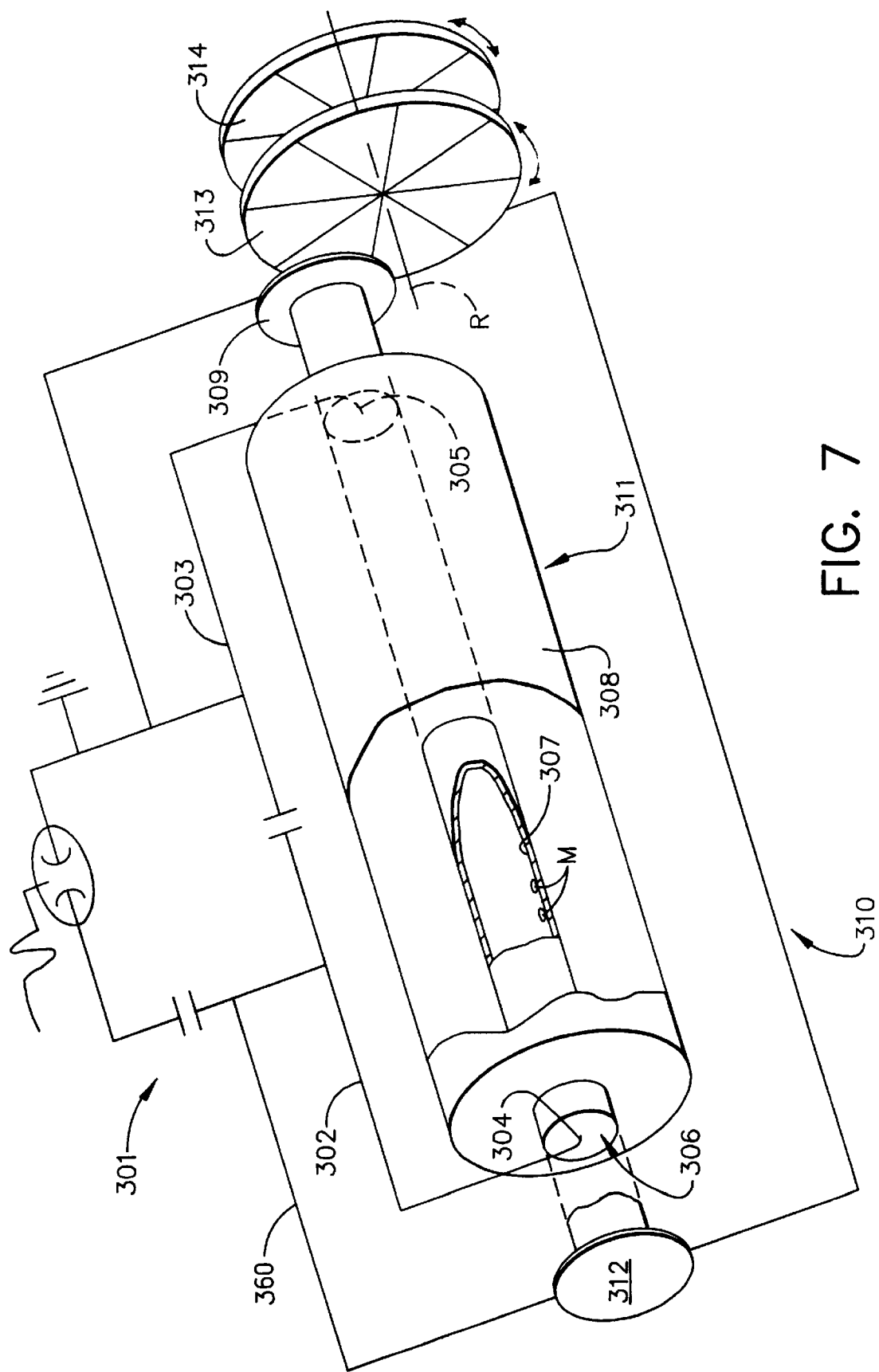
FIG. 7 is a partially broken-away enlarged perspective view of a metal vapor laser system made in accordance with the present invention.

FIG. 7 illustrates a partially schematic and broken-away perspective view of a metal vapor laser system 310 including an active laser gain medium 311 located within a vacuum housing or envelope 360. A means (e.g., 301) is provided for exciting the active laser gain medium 311, such as in the form an electric power source connected via lines 302 and 303 to a pair of oppositely disposed electrodes 304 and 305. Electrodes 304 and 305 are preferably situated adjacent opposite ends of an internal tube 306 along which a charge of one or more metals (e.g., M), such as barium, thulium, samarium, copper, gold, etc. to be vaporized therewithin, is placed. Tube 306 may preferably be formed of refractory material (e.g., ceramic material) to accommodate the relatively high heats required to vaporize the metal charges.

Tube 306 comprises substantially cylindrical tubular wall 307 and preferably houses an inert gas. Electrical discharge from means 301 runs between electrodes 304 and 305 along tube 306, which is preferably thermally insulated (e.g., via insulation jacket 308) and the heat generated by the pulsed discharge raises the temperature of the tubes sufficiently to vaporize metal charge M loaded along its length. An inert buffer gas (e.g., helium or argon) preferably fills evacuated tube 306, and provides an "atmosphere" within which vaporized metal can be suspended. Continuation of the pulsed electric discharge excites the metal vapor and induces lasing.

As an example, the short, high peak power pulses of laser radiation produced by laser system 310 utilizing barium vapor generates pulses of between about 20 and 50 nsec, with peak powers on the order of approximately 100 kW. Due to the relatively short laser pulse lengths in metal vapor lasers, no Q-switching or mode-locking mechanism is required for temporal control. Moreover, the barium vapor laser produces radiation at three strong wavelengths, i.e. approximately 1.13 microns, 1.5 microns and 2.55 microns. At proper intensities, the 1.13 micron line is suitable for surgical photocoagulation, whereas both of the 1.5 and 2.55 micron lines are useful for tissue cutting. In fact, the 1.5 micron wavelength cuts in a way comparable to the HO:YAG laser system, yet can be transmitted along inexpensive, high OH silica fibers. The 1.13 microns wavelength penetrates deeply into tissue and provides for excellent hemostasis during surgery, and is also transmissible through the high OH silica fibers. Non-silica fiber optics can be utilized to transmit light energy with wavelengths greater than about 2.4 microns (e.g., the 2.55 micron line).

While many laser media produce laser radiation at a plurality of wavelengths depending upon the conditions of excitation and the like, most lasers have heretofore been designed to extract only a single wavelength line from the laser. In order to utilize a plurality of wavelengths from a metal vapor laser, for example, it will also be preferred to provide selective control of the absolute intensities of two or more wavelength components in a single laser output. Such control might be attempted by the insertion of elements to preferentially absorb at predetermined wavelengths along the optical path, or by altering the inert gas pressure or temperature of the vapor plasma tube (e.g., tube 306). Selective control by absorption is, however, difficult, and can lead to a significant loss in the total output power of the laser. Similarly, while altering the temperature or pressure of the laser gain medium in a gas laser can alter the relative ratio of intensities of output wavelengths, rapid changes in the temperature of the plasma tube, or in the pressure of the gas, are difficult to achieve in a controlled, uniform, and repeatable fashion, and may significantly compromise the overall efficiency and operation of the laser.

A more preferred manner of selectively controlling relative intensities of the output wavelengths in a metal vapor laser system (e.g., 310) utilizes the concept of gain saturation. Particularly, one or more variable reflectivity output coupling mirrors (e.g., 313 and/or 314) can be utilized to selectively saturate the lowest energy levels involved in the lasing transitions. As an example, commercially available barium vapor laser systems are generally configured to operate with outputs of 1.13, 1.5, and/or 2.55 microns. These wavelengths represent the strongest laser transitions in neutral barium vapor. In a barium vapor laser optimized to output radiation at 1.13 and 1.5 microns, the actual lasing transitions involved are as follows:

$6p^1P_1^0 \rightarrow 5d^3D_2$ (which produces the 1.13 micron wavelength)

$6p^1P_1^0 \rightarrow 5d^1D_2$ (which produces the 1.5 micron wavelength)

As can be seen, the two transitions share the same upper energy level, and the 1.13 micron transition will have the lower of the two final energy levels. If this lower energy level becomes saturated, the rate of the 1.13 micron transition will drop off dramatically. This same phenomenon occurs when the temperature of the barium vapor is increased, as the higher gas temperature results in population saturation of the $5d^3D_2$ level, resulting in a decrease in the 1.13 micron wavelength output. If the gas temperature is increased further, the $5d^1D_2$ energy level eventually reaches population saturation, and the 1.5 micron wavelength output vanishes as well.

Consequently, the saturation control mechanism involved herein requires the maintenance of a large population in the $5d^3D_2$ level by use of cavity mirrors (e.g., mirror 312 and variable mirror 313) which are highly reflective at the 1.13 micron wavelength. Particularly, if output coupling mirror 313 has high reflectivity at the 1.13 micron wavelength, and lower reflectivity at 1.5 microns, it will allow laser 310 to output at the 1.5 micron wavelength while the 1.13 micron field continues to build in intensity within the cavity. As the intensity of the 1.13 micron field builds up in the resonant cavity (and as the $5d^3D_2$ level saturates), the preferred lasing transition will become the $6p^1P_1^0 \rightarrow 5d^1D_2$ transition, resulting in a high output at the 1.5 micron line as well as a lower output at the 1.13 micron wavelength. In this way, output at multiple wavelengths with controlled intensities can be achieved without wasting total laser output. Additionally, this approach allows constant operation of the laser at full power, and relatively fast and reliable alterations or changes in the relative intensities of output wavelengths.

Figure 8:
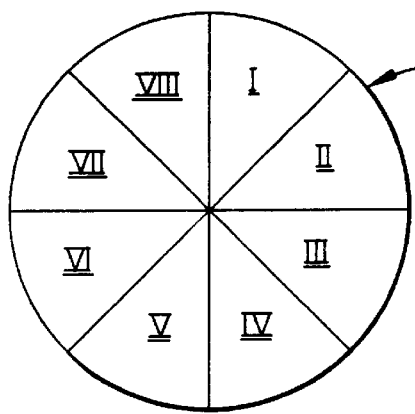
FIG. 8 is a top plan view of a variably reflective output-coupler mirror which can be used in a metal vapor laser as illustrated in FIG. 7.

FIG. 8 shows an end view of a variable reflectivity output-coupler mirror (e.g., 313–314) which comprises a plurality of partitioned zones having predetermined reflectivity at particular wavelengths. For example, Zone I may be 100% reflective at 1.13 microns, while Zone II is 99% reflective, Zone III 98% reflective, Zone IV 95% reflective, Zone V 90%, Zone VI 70%, Zone VII 60% and Zone VIII 50% reflective at 1.13 microns. Similarly, another variable reflectivity output-coupler mirror could have similar zones of varying reflectivity with respect to the 1.5 micron wavelength. Such variable output-coupler mirrors might be rotatably arranged along an axis of rotation (e.g. R) for convenient rotatable alignment with laser output window 309. As will be understood, the number and reflectivity of variable output-coupler devices or mirrors 313 and 314 would be determined based upon the particular metal(s) utilized in laser system 310, and the output wavelengths and intensities to be controlled.

Figure 9:
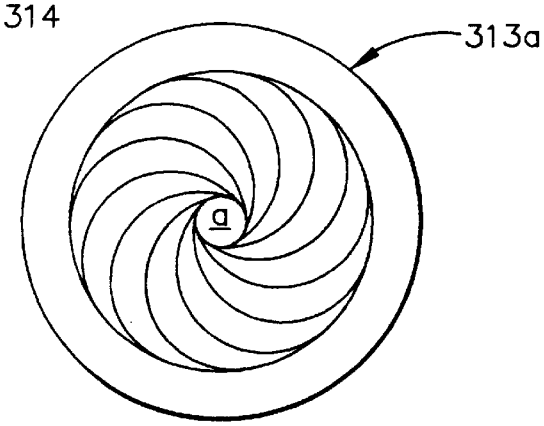
FIG. 9 is a top plan view of a continuously variable aperture site or iris which can alternately be used as a variably reflective output-coupler device in a vapor laser of the present invention.

It is contemplated that one or more variable reflectivity output-coupler mirrors (e.g., 313, 314) could be automatically controlled by a controller (not shown) to provide a variable attenuator which automatically responds to preset wavelength selections, intensity requirements, or other user input. FIG. 9 illustrates a continuously variable aperture site or iris 313a having a plurality of reflectively coated leaves which can adjust the size of the aperture (a) through which laser radiation passes. As an example, a pair of irises 313a could be used in series, where the first is coated for high reflectivity at a first wavelength (e.g., the 1.13 line) and high transmissivity at a second wavelength (e.g., the 1.5 line), and the second iris is coated in an opposite manner. If the second iris is then left open, while the first is closed, maximum output at the second wavelength is achieved. Similarly, if both irises are closed, neither wavelength would emit. Each iris can be under microprocessor control for accurate and automatic adjustment.

In an alternate preferred embodiment, metal vapor laser system 310 can be provided with a plurality of metal charges to provide multiple-metal vapors within plasma tube 306, and/or can be used in conjunction with other laser conversion devices (e.g., OPO crystals) to enable the conversion of at least a portion of its radiation to additional useful wavelengths. Any of the metal vapor laser systems could also be used to pump another laser gain medium to provide additional wavelengths. For example, a laser which would have advantageous use in laser surgery might incorporate a combination barium-thulium vapor, wherein the barium vapor would provide radiation at 1.13 microns such as for photocoagulation, while the strong thulium output line at about 1.96 microns would provide for precise laser cutting of tissue. All other lines of energy created by this combination of metal vapors could be removed from the output by use of the appropriate variable reflectivity output-couplers, as described.

Similarly, a combination samarium and barium vapor laser could provide superior laser cutting with outputs at 2.96 and 2.7 microns (samarium) and photocoagulation at 1.13 microns (barium). Likewise, PDT applications could be accommodated by a combination of gold vapor (with output at 0.628 nm) and barium vapor (with its output at 1.13 microns). In each of these applications, means (e.g., variable output-couplers 313, 314) for controlling the absolute intensities of each wavelength component would be provided to appropriately "tune" the multiple wavelength output for optimum efficiency in a particular medical procedure.

Figure 10:
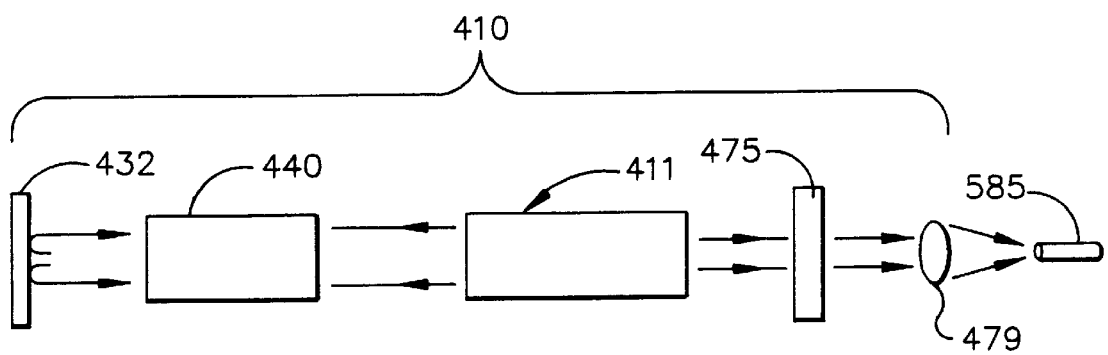
FIG. 10 is a schematic diagram of a metal vapor laser system including a conversion medium for converting at least a portion of the laser radiation from the laser gain medium to one or more additional medically useable wavelengths.

A laser system 410 is illustrated in FIG. 10 as including a metal vapor laser gain medium 411 similar to medium 311 described above, and a means 440 for converting at least a portion of the laser radiation produced by the gain medium 411 into one or more additional wavelengths. For example, converting means 440 could comprise an OPO conversion crystal such as KTP, or another laser gain medium, either within or outside of cavity 410. Where the active laser gain medium 411 comprises barium vapor pumping at the 1.5 and 1.13 microns wavelengths, a KTP crystal oriented at a 90° phase matching angle would convert a portion of the 1.13 line into radiation at about 1.73 microns and about 3.27 microns, and would convert a portion of the 1.5 line into radiation at about 2.78 microns and about 3.25 microns. Cavity mirror 432 would be highly reflective at all wavelengths, while mirror 475 would preferably be highly reflective at the 1.5 and 1.73 microns wavelengths, and highly transmissive at the 1.13, 2.78, 3.25 and 3.27 microns wavelengths. As discussed above the 1.13 line is good for photocoagulation procedures, and the remaining three lines (2.78, 3.25 and 3.27 microns) are good surgical cutting wavelengths.

The high gain of the metal vapor lasers (e.g., barium and copper) results in almost no insertion power loss, the 90° angle results in relatively efficient OPO conversion, and a number (e.g., 4) of medically useful wavelengths are simultaneously and coaxially produced. Moreover, the mirror coating combinations are relatively simple, thereby making such a system quite valuable and adaptable to a variety of applications.

Alternatively, coherent pumping could be utilized by aligning a metal vapor gain medium (e.g., Barium vapor) with an Erbium YAG laser crystal ($Er^{3+}$:YAG), and separating the two by a mirror highly reflective at the 1.13 micron wavelength. The Barium vapor medium would produce both 1.13 and 1.5 microns radiation, whereby the 1.5 microns output pumps the $Er^{3+}$:YAG crystal causing lasing at 2.94 microns. A totally reflective back mirror and a mirror partially transmissive at the 1.13 and 2.94 microns wavelengths, and highly reflective at 1.5 microns could be used to provide a resonant cavity for the setup. The output of such a system would provide coaxial radiation at both 2.94 and 1.13 microns, a combination medically useable for simultaneous surgical cutting and coagulation.

Further adaptions of the laser systems and methods described herein can be accomplished by appropriate modifications by one of ordinary skill in the art without departing from the scope of the present invention. Accordingly, the scope of the present invention should be considered in terms of the following claims, and is understood not to be limited to the details of structure and operation shown an described in the specification and drawings.

I claim:

1. A multiple wavelength laser system for medical applications involving tissue comprising water and a predetermined chromophore, said system comprising:

an active laser gain medium located within a resonant cavity, said medium comprising metal vapor;

means for exciting said active laser gain medium to produce a plurality of lasing energy level transitions and resulting laser radiation at a plurality of wavelengths;

means for coaxially transmitting laser radiation at a plurality of wavelengths at predetermined intensities from said laser system for simultaneous use in a medical procedure, a first of said wavelengths being in a range of wavelengths having greater absorption by said predetermined chromophore than by water, and a second of said wavelengths being in a range of wavelengths having greater absorption by water than by said predetermined chromophore, and means for controlling populations of multiple lasing energy level transitions to thereby control relative intensities among the coaxially transmitted wavelengths, thereby providing a means for controlling total intensities of such transmitted wavelengths.

2. The laser system of claim 1, wherein said means for coaxially transmitting said plurality of wavelengths from said laser system comprises a fiber optic device.

3. The laser system of claim 1, further comprising means for converting at least a portion of the laser radiation produced by said laser gain medium to at least one additional wavelength.

4. The laser system of claim 1, wherein said means for controlling populations of multiple lasing energy level transitions comprises a continuously variable dichroic aperture site or iris device.

5. The laser system of claim 1 wherein said predetermined chromophore is oxyhemoglobin.

6. The laser system of claim 1 wherein said predetermined chromophore is deoxyhemoglobin.

7. The laser system of claim 1 wherein said predetermined chromophore is melanin.

8. The laser system of claim 1, wherein said laser gain medium comprises barium vapor.

9. The laser system of claim 8, further comprising means for producing a third wavelength which is also in a range of wavelengths that is readily absorbed by either water or said predetermined chromophore.

10. The laser system of claim 1, wherein said means for controlling the population of at least one of said lasing energy level transitions comprises a variable reflectivity output-coupler optic.

11. The laser system of claim 10, wherein said variable reflectivity output-coupler optic comprises a plurality of substantially independent zones, and wherein said optic can be moved to align one of said zones with said resonant cavity.

12. The laser system of claim 11, wherein said output-coupler optic can be rotatable arranged for selective alignment with said laser system to control the wavelength intensities as desired.

13. The laser system of claim 1, wherein said laser gain medium comprises a plurality of different metal vapors.

14. The laser system of claim 13, wherein said metal vapors comprise barium, and at least one additional metal chosen from the group of thulium and samarium.

15. The laser system of claim 14, wherein said metal vapors include barium and thulium, and wherein said second wavelength is approximately 1.96 microns, and said first wavelength is approximately 1.13 microns.

16. The laser system of claim 14, wherein said metal vapors include barium and samarium, and wherein said second wavelength is in a range between about 2.7 and 3.25 microns, and said first wavelength is approximately 1.13 microns.

17. A multiple wavelength metal vapor laser system for medical applications involving the targeting of a particular drug, agent or other photosensitive substance for treatment in tissue comprising water and a predetermined chromophore, said laser system comprising:

an active laser gain medium comprising a plurality of metal vapors;

means for exciting said laser gain medium to produce a plurality of lasing energy level transitions and resulting laser radiation at a plurality of wavelengths;

means for coaxially transmitting laser radiation at a plurality of wavelengths from said laser system for simultaneous use in a medical procedure, a first of said wavelengths being in a range of wavelengths having greater absorption by either water or said predetermined chromophore than by the particular photosensitive substance targeted in a medical application, and a second of said wavelengths being in a range of wavelengths having greater absorption by the particular photosensitive substance targeted in said medical application than by water or said predetermined chromophore; and means for controlling populations of multiple lasing energy level transitions to thereby control relative intensities among said first and second wavelengths, thereby providing a means for controlling total intensities of said first and second wavelengths.

18. The laser system of claim 17, wherein said laser gain medium comprises barium vapor and at least one metal vapor from the group of thulium and samarium.

19. The laser system of claim 17, wherein said means for controlling populations of multiple lasing energy level transitions comprises a variable reflectivity output-coupler optic.

20. The laser system of claim 17, wherein said means for controlling populations of multiple lasing energy level transitions comprises a continuously variable dichroic aperture site or iris device.

21. The laser system of claim 20, further comprising a microprocessor control for accurate and automatic adjustment of said iris.

22. The laser system of claim 20, further comprising a plurality of irises arranged in series.

23. A multiple wavelength metal vapor laser system for medical applications involving tissue comprising water and a predetermined chromophore, said laser system comprising:
- an active laser gain medium comprising barium metal vapor;
- means for exciting said active laser gain medium to produce a plurality of lasing energy level transitions and resulting laser radiation at a plurality of wavelengths;
- means for coaxially transmitting laser radiation from said laser system at a plurality of wavelengths at predetermined intensities for simultaneous use in a medical procedure, a first of such wavelengths being in a range of wavelengths having greater absorption by said predetermined chromophore than by water, and a second of such wavelengths being in a range of wavelengths having greater absorption by water than by said predetermined chromophore; and
- means for controlling populations of multiple lasing energy level transitions to thereby control relative intensities among said first and second wavelengths, thereby providing a means for controlling total intensities of said first and second wavelengths.

24. The laser system of claim 23, further comprising means for converting at least a portion of said laser radiation produced by said laser gain medium to at least one additional wavelength.

25. The laser system of claim 23, wherein said laser gain medium produces radiation at a first wavelength of approximately 1.13 microns and additional wavelengths of approximately 1.5 microns and 2.55 microns.

26. The laser system of claim 23, wherein said laser gain medium comprises barium vapor and thulium vapor, and produces a first wavelength of approximately 1.13 microns, and a second wavelength of approximately 1.96 microns.

27. The laser system of claim 23, wherein said laser gain medium comprises barium vapor and samarium vapor, and produces a first wavelength of approximately 1.13 microns, and a second wavelength is chosen from the group of wavelength ranges centered around approximately 2.96 microns and approximately 2.7 microns having high absorption by water relative to its absorption by Hemoglobin or other tissue chromophores.

28. The laser system of claim 23, wherein said means for controlling populations of multiple lasing energy level transitions comprises a variable reflectivity output-coupler optic.

29. The laser system of claim 23, wherein said means for controlling populations of multiple lasing energy level transitions comprises a continuously variable dichroic aperture site or iris device.

30. A multiple wavelength laser system for medical applications involving tissue comprising water and a predetermined chromophore, said system comprising:
- an active laser gain medium located within a resonant cavity, said medium comprising metal vapor;
- means for exciting said active laser gain medium to produce a plurality of lasing energy level transitions and resulting laser radiation at a plurality of wavelengths;
- a fiber optic device for coaxially transmitting laser radiation at a plurality of wavelengths at predetermined intensities from said laser system for simultaneous use in a medical procedure, a first of said wavelengths being in a range of wavelengths having greater absorption by said predetermined chromophore than by water, and a second of said wavelengths being in a range of wavelengths having greater absorption by water than by said predetermined chromophore; and
- an output coupler for controlling populations of multiple lasing energy level transitions to thereby control relative intensities among the coaxially transmitted wavelengths, thereby providing a means for controlling total intensities of such transmitted wavelengths.

* * * * *